(12) United States Patent
Benke

(10) Patent No.: US 9,415,053 B2
(45) Date of Patent: *Aug. 16, 2016

(54) SOLID, ORALLY ADMINISTRABLE PHARMACEUTICAL COMPOSITION

(71) Applicant: Bayer Intellectual Property GmbH, Monheim (DE)

(72) Inventor: Klaus Benke, Bergisch Gladbach (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/250,863

(22) Filed: Apr. 11, 2014

(65) Prior Publication Data

US 2014/0248349 A1 Sep. 4, 2014

Related U.S. Application Data

(63) Continuation of application No. 10/580,711, filed as application No. PCT/EP2004/012897 on Nov. 13, 2004, now abandoned.

(30) Foreign Application Priority Data

Nov. 27, 2003 (DE) .................................. 103 55 461

(51) Int. Cl.
*A61K 9/28* (2006.01)
*A61K 31/5377* (2006.01)
*A61K 9/16* (2006.01)
*A61K 9/20* (2006.01)
*A61K 9/48* (2006.01)

(52) U.S. Cl.
CPC ........... *A61K 31/5377* (2013.01); *A61K 9/1611* (2013.01); *A61K 9/1617* (2013.01); *A61K 9/1623* (2013.01); *A61K 9/1652* (2013.01); *A61K 9/1682* (2013.01); *A61K 9/2009* (2013.01); *A61K 9/2013* (2013.01); *A61K 9/2018* (2013.01); *A61K 9/2054* (2013.01); *A61K 9/2077* (2013.01); *A61K 9/2095* (2013.01); *A61K 9/2893* (2013.01); *A61K 9/4808* (2013.01)

(58) Field of Classification Search
CPC ............ A61K 31/5377; A61K 9/1611; A61K 9/1617; A61K 9/1623; A61K 9/1652; A61K 9/1682; A61K 9/2009; A61K 9/2013; A61K 9/2018; A61K 9/2054; A61K 9/2077; A61K 9/2095; A61K 9/2893; A61K 9/4808
See application file for complete search history.

(56) References Cited

U.S. PATENT DOCUMENTS

| | | | |
|---|---|---|---|
| 2,811,555 A | 10/1957 | Larive et al. | |
| 3,279,880 A | 10/1966 | Straley et al. | |
| 4,128,654 A | 12/1978 | Fugitt et al. | |
| 4,250,318 A | 2/1981 | Dostert et al. | |
| 4,327,725 A | 5/1982 | Cortese et al. | |
| 4,344,934 A * | 8/1982 | Martin et al. ................. | 514/462 |
| 4,500,519 A | 2/1985 | Lormeau et al. | |
| 4,705,779 A | 11/1987 | Madi-Szabo et al. | |
| 4,724,141 A | 2/1988 | Schmidt et al. | |
| 4,765,989 A | 8/1988 | Wong et al. | |
| 4,948,801 A | 8/1990 | Carlson et al. | |
| 4,977,173 A | 12/1990 | Brittelli et al. | |
| 5,002,937 A | 3/1991 | Bosies et al. | |
| 5,254,577 A | 10/1993 | Carlson et al. | |
| 5,349,045 A | 9/1994 | Jiang | |
| 5,532,255 A | 7/1996 | Raddatz et al. | |
| 5,561,148 A | 10/1996 | Gante et al. | |
| 5,565,571 A | 10/1996 | Barbachyn et al. | |
| 5,624,687 A | 4/1997 | Yano et al. | |
| 5,654,428 A | 8/1997 | Barbachyn et al. | |
| 5,654,435 A | 8/1997 | Barbachyn et al. | |
| 5,688,792 A | 11/1997 | Barbachyn et al. | |
| 5,756,732 A | 5/1998 | Barbachyn et al. | |
| 5,792,765 A | 8/1998 | Riedl et al. | |
| 5,801,246 A | 9/1998 | Barbachyn et al. | |
| 5,827,857 A | 10/1998 | Riedl et al. | |
| 5,910,504 A | 6/1999 | Hutchinson et al. | |
| 5,922,708 A | 7/1999 | Riedl et al. | |
| 5,929,248 A | 7/1999 | Barbachyn et al. | |
| 5,935,724 A | 8/1999 | Spillman et al. | |
| 5,972,947 A | 10/1999 | Tsaklakidis et al. | |
| 5,977,373 A | 11/1999 | Gadwood et al. | |
| 5,998,406 A | 12/1999 | Hester et al. | |
| 6,069,160 A | 5/2000 | Stolle et al. | |
| 6,074,670 A | 6/2000 | Stamm et al. | |

(Continued)

FOREIGN PATENT DOCUMENTS

| | | |
|---|---|---|
| AU | 744002 | 2/2002 |
| DE | 2836305 A1 | 3/1979 |

(Continued)

OTHER PUBLICATIONS

Gao et al. International Journal Pharmaceutics. 2002; 237: 1-14.*
Letter from Bayer Pharma Aktiengesellschaft to European Patent Office ("EPO") dated Sep. 26, 2011 containing grounds for appeal of Opposition Division's partial revocation of Bayer's EP Patent 1 689 370 B1.
Letter from ratiopharm GmbH to the EPO dated Sep. 26, 2011 containing grounds for appeal of Opposition Division's upholding of Bayer's auxiliary request 2 in the Opposition to EP Patent 1 689 370.

(Continued)

*Primary Examiner* — Johann R Richter
*Assistant Examiner* — David Browe
(74) *Attorney, Agent, or Firm* — Buchanan Ingersoll & Rooney PC

(57) ABSTRACT

The present invention relates to a process for the preparation of a solid, orally administrable pharmaceutical composition, comprising 5-chloro-N-({(5S)-2-oxo-3-[4-(3-oxo-4-morpholinyl)-phenyl]-1,3-oxazolidin-5-yl}-methyl)-2-thiophenecarboxamide in hydrophilized form, and its use for the prophylaxis and/or treatment of diseases.

24 Claims, No Drawings

(56) References Cited

U.S. PATENT DOCUMENTS

| | | | |
|---|---|---|---|
| 6,159,997 A | 12/2000 | Tsujita et al. | |
| 6,218,413 B1 | 4/2001 | Hester et al. | |
| 6,251,869 B1 | 6/2001 | Bohanon | |
| 6,265,178 B1 | 7/2001 | Martin, Jr. | |
| 6,281,210 B1 | 8/2001 | Hester, Jr. | |
| 6,294,201 B1 | 9/2001 | Kettelhoit et al. | |
| 6,303,626 B1 | 10/2001 | Abramovici et al. | |
| 6,514,529 B2 * | 2/2003 | Yamamoto et al. | 424/465 |
| 6,589,552 B2 | 7/2003 | Stamm et al. | |
| 6,805,881 B1 | 10/2004 | Kanikanti et al. | |
| 6,818,243 B2 | 11/2004 | Nagashima et al. | |
| 7,034,017 B2 | 4/2006 | Straub et al. | |
| 7,045,631 B2 | 5/2006 | Rosentreter et al. | |
| 7,078,417 B2 | 7/2006 | Rosentreter et al. | |
| 7,109,218 B2 | 9/2006 | Rosentreter et al. | |
| 7,129,255 B2 | 10/2006 | Rosentreter et al. | |
| 7,157,456 B2 | 1/2007 | Straub et al. | |
| 2001/0029351 A1 | 10/2001 | Falotico et al. | |
| 2001/0046987 A1 | 11/2001 | Hester et al. | |
| 2003/0153610 A1 * | 8/2003 | Straub et al. | 514/376 |
| 2003/0161882 A1 | 8/2003 | Waterman | |
| 2004/0092480 A1 | 5/2004 | Fujinaga et al. | |
| 2004/0162427 A1 | 8/2004 | Rosentreter et al. | |
| 2004/0242660 A1 | 12/2004 | Straub et al. | |
| 2005/0064006 A1 | 3/2005 | Perzborn et al. | |
| 2005/0182055 A1 | 8/2005 | Berwe et al. | |
| 2005/0261502 A1 | 11/2005 | Rosentreter et al. | |
| 2006/0154969 A1 | 7/2006 | Rosentreter et al. | |
| 2006/0258724 A1 | 11/2006 | Straub et al. | |
| 2007/0026065 A1 | 2/2007 | Benke et al. | |
| 2007/0149522 A1 | 6/2007 | Thomas | |
| 2008/0026057 A1 | 1/2008 | Benke | |
| 2008/0090815 A1 | 4/2008 | Straub et al. | |
| 2008/0200674 A1 | 8/2008 | Straub et al. | |
| 2010/0151011 A1 | 6/2010 | Benke | |

FOREIGN PATENT DOCUMENTS

| | | |
|---|---|---|
| DE | 3417113 A1 | 11/1984 |
| DE | 196 04 223 A1 | 8/1997 |
| DE | 19962924 A1 | 7/2001 |
| DE | 10105989 A1 | 8/2002 |
| DE | 10129725 A1 | 1/2003 |
| DE | 10355461 A1 | 6/2005 |
| EP | 0 127 902 A2 | 12/1984 |
| EP | 0 316 594 A1 | 5/1989 |
| EP | 0 352 781 A2 | 1/1990 |
| EP | 0350002 A1 | 1/1990 |
| EP | 0623615 A1 | 11/1994 |
| EP | 0645376 A1 | 3/1995 |
| EP | 0738726 A1 | 10/1996 |
| EP | 0 785 200 A2 | 7/1997 |
| EP | 0930076 A1 | 7/1999 |
| EP | 0950386 A2 | 10/1999 |
| GB | 2140687 | 12/1984 |
| JP | S56-11061 A | 2/1981 |
| KR | 0179343 B1 | 3/1999 |
| KR | 20010040484 A | 5/2001 |
| KR | 20030076634 A | 9/2003 |
| WO | WO-93/09103 A1 | 5/1993 |
| WO | WO-93/23384 A1 | 11/1993 |
| WO | WO-97/03072 A1 | 1/1997 |
| WO | WO-97/09328 A1 | 3/1997 |
| WO | WO-97/10223 A1 | 3/1997 |
| WO | WO-98/00116 | 1/1998 |
| WO | WO-98/01446 A1 | 1/1998 |
| WO | WO-98/54161 A1 | 12/1998 |
| WO | WO-99/02525 A1 | 1/1999 |
| WO | WO-99/03846 A1 | 1/1999 |
| WO | WO-99/21535 A1 | 5/1999 |
| WO | WO-99/24428 A1 | 5/1999 |
| WO | WO-99/29688 A1 | 6/1999 |
| WO | WO-99/31092 A1 | 6/1999 |
| WO | WO-99/37304 A1 | 7/1999 |
| WO | WO-99/37630 A1 | 7/1999 |
| WO | WO-99/37641 A1 | 7/1999 |
| WO | WO-99/40094 A1 | 8/1999 |
| WO | WO-99/59616 A1 | 11/1999 |
| WO | WO-00/16748 A1 | 3/2000 |
| WO | 0032189 A1 | 6/2000 |
| WO | WO-01/42242 A1 | 6/2001 |
| WO | WO-01/44212 A1 | 6/2001 |
| WO | WO-01/46185 A1 | 6/2001 |
| WO | 01/47919 A1 | 7/2001 |
| WO | WO-01/47919 A1 | 7/2001 |
| WO | WO-01-47949 A1 | 7/2001 |
| WO | WO-02/15940 A2 | 2/2002 |
| WO | WO-0215940 A2 | 2/2002 |
| WO | WO-02/25210 A1 | 3/2002 |
| WO | WO-02/38126 A2 | 5/2002 |
| WO | WO-0238126 A2 | 5/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/000256 A1 | 1/2003 |
| WO | WO-03/008384 A1 | 1/2003 |
| WO | WO-03/035133 A1 | 5/2003 |
| WO | WO-03/053441 A1 | 7/2003 |
| WO | WO-2004/060887 A1 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Letter from ratiopharm GmbH to the EPO dated May 9, 2012 in the appeal of the Opposition Division's decision in EP Patent 1 689 370.

Letter from Bayer Pharma Aktiengesellschaft dated May 9, 2012 in the appeal of the Opposition Division's decision in EP Patent 1 689 370.

Letter from Bayer Pharma Aktiengesellschaft dated Aug. 31, 2012 in the appeal of the Opposition Division's decision in EP Patent 1 689 370.

Parikh, D. M. (editor), "Handbook of Pharmaceutical Granulation Technology", 1997, vol. 81, pp. 7-9, publisher: Marcel Dekker, Inc., New York.

Von Bruchbausen, F., "Hagers Handbuch der pharmazeutischen Praxis", 5$^{th}$ edition, Heidelberg, 1991, pp. 728-734.

Ohm, A., "Critical Manufacturing Variables and In Vitro Dissolution Tests in View of In Vivo Performance", in Bio-International 2-Bioavailability, Bioequivalence and Pharmacokinetic Studies, Blume H.H. and Midha, K.K. (eds.), mepharm, Stuttgart, 1995, pp. 261-279.

Gennaro, A. R. (ed.), "Remington: The Science and Practice of Pharmacy," 2000, 20$^{th}$ Edition, p. 865.

"FIP Guidelines for Dissolution Testing of Solid Oral Products," *Pharm. Ind.* 59, No. 9, 1997, pp. 760-766.

FDA, Center for Drug Evaluation and Research, *Guidance for Industry*, "Dissolution Testing of Immediate Release Solid Oral Dosage Forms", 1997, pp. 1-11.

Shah, V. P., "In Vitro Dissolution Profile of Water-Insoluble Drug Dosage Forms in the Presence of Surfactants," *Pharmaceutical Research*, 1989, vol. 6, No. 7, pp. 612-618.

Klein. S., "The Use of Biorelevant Dissolution Media to Forecast the In Vivo, Performance of a Drug," *The AAPS Journal*, 2010, vol. 12, No. 3, pp. 397-406.

Bono, F., et al., "Human Umbilical Vein Endothelial Cells Express High Affinity Receptors for Factor Xa", Journal of Cellular Physiology, 1997, vol. 172, pp. 36-43.

(56) References Cited

OTHER PUBLICATIONS

Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.
Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.
Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.
Altieri, D. C., et al., "Identification of Effector Cell Protease Receptor-1", The Journal of Immunology, 1990, vol. 145, No. 1, pp. 246-253.
Coughlin, S. R., "Thrombin Signalling and Protease-Activated Receptors", Nature, 2000, vol. 407, pp. 258-264.
Ornstein, D. L., et al., "Cancer, Thrombosis, and Anticoagulants", Current Opinion in Pulmonary Medicine, 2000, vol. 6, pp. 301-308.
Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409.
Herault, J-P., et al., "Activation of Human Vascular Endothelial Cells by Factor Xa: Effect of Specific Inhibitors", Biochemical Pharmacology, 1999, vol. 57, pp. 603-610.
Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.
Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.
Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.
Howells, G. L., et al., "Proteinase-Activated Receptor-2: Expression by Human Neutrophils", Journal of Cell Science, 1997, vol. 110, pp. 881-887.
Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.
Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.
Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.
Zhang, Y., et al., "Tissue Factor Controls the Balance of Angiogenic and Antiangiogenic Properties of Tumor Cells in Mice", J. Clin. Invest., 1994, vol. 94, pp. 1320-1327.
Green, D., et al., "Lower Mortality in Cancer Patients Treated with Low-Molecular-Weight Versus Standard Heparin", The Lancet, 1992, vol. 339, p. 1476.
Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.
Kakkar, A. K., et al., "Antithrombotic Therapy in Cancer", BMJ, 1999, vol. 3318, pp. 1571-1572.
Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.
Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.
Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.
Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.
Camerer, E., et al., "Tissue Factor- and Factor X-dependent Activation of Protease-Activated Receptor 2 by Factor VIIa", PNAS, 2000, vol. 97, No. 10, pp. 5255-5260.
Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.
Lindner, J. R., et al., "Delayed Onset of Inflammation in Protease-Activated Receptor-2-Deficient Mice", The Journal of Immunology, 2000, pp. 6504-6510.
Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.
Molino, M., et al., "Endothelial Cell Thrombin Receptors and PAR-2", The Journal of Biological Chemistry, 1997, vol. 272, No. 17, pp. 11133-11141.
Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.
Watson, D. J., et al., "Heparin-Binding Properties of the Amyloidogenic Peptides Aβ and Amylin", The Journal of Biological Chemistry, 1997, vol. 272, No. 50, pp. 31617-31624.
Tuszynski, G. P., et al., "Isolation and Characterization of Antistasin", The Journal of Biological Chemistry, 1987, vol. 262, No. 20, pp. 9718-9723.
Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.
Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.
Abendschein, D. R., et al., "Inhibition of Thrombin Attenuates Stenosis After Arterial Injury in Minipigs", JACC, 1996, vol. 28, No. 7, pp. 1849-1855.
Carmeliet, P., et al., "Gene Manipulation and Transfer of the Plasinogen and Coagulation System in Mice", Seminars in Thrombosis and Hemostasis, 1996, vol. 22, No. 6, pp. 525-542.
Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.
Bevilacqua, M. P., et al., "Inducible Endothelial Functions in Inflammation and Coagulation", Seminars in Thrombosis and Hemostasis, 1987, vol. 13, No. 4, pp. 425-433.
Riedl, B., et al., "Recent Developments with Oxazolidinone Antibiotics", Exp. Opin. Ther. Patents, 1999, vol. 9, No. 5, pp. 625-633.
Barbachyn, M.R., et al., "Identification of Novel Oxazolidinone (U-100480) with Potent Antimycobacterial Activity", J. Med. Chem., 1996, vol. 39, pp. 680-685.
Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.
Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.
Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.

(56) References Cited

OTHER PUBLICATIONS

Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.
Meng, K., et al., "Effect of Acetylsalicyclic Acid of Experimentally Induced Arterial Thrombosis in Rats", Naunyn-Schmiedeberg's Arch. Pharmacol.,1977, vol. 301, pp. 115-119.
Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.
Shakespeare, W. C., et al., "Palladium-Catalyzed Coupling of Lactams with Bromobenzenes", Tetrahedron Lett., 1999, vol. 40, pp. 2035*2038.
Renger, B., et al., "Direkte N-Arylierung von Amiden: Eine Verbesserung der Goldberg-Reaktion", Synthesis, 1985, pp. 856-860.
Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11 , pp. 2225-2229.
Pfeil, E., et al., "β-Aminoäthylierung von Indol und 2-methylindol", Angew Chem., 1967, vol. 79, No. 4, pp. 188-189.
Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.
Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.
Reppe, et al., "N-p-Merthoxyphenyl-pyrrolidon", Justus Liebigs Ann. Chem., 1955 vol. 596, p. 208.
Luvalle, J.E., et al., "Oxidation Processes. XXI.[1] The Autoxidation of the ρ-Phenylenediamines", J. Am. Chem. Soc., 1948, vol. 70, pp. 2223-2233.
Snyder, H.R., et al., "Imidazo[4,5f]quinolines III: Antibacterial 7-Methyl-9-(substituted Arylamino)imidazo[4,5-f]quinolines", J. Pharm. Sci., 1977, vol. 66, pp. 1204-1406.
Adams, R., et al., "Sulfanilamide Derivatives. I", J. Am. Chem. Soc. 1939, vol. 61, pp. 2342-2349.
Khanna, I.K. , et al., "1,2-Diarylpyrroles as Potent and Selective Inhibitors of Cyclooxygenase-2", J. Med. Chem., 1997, vol. 40 , pp. 1619-1633.
Gutcait, A., et al., "Studies on Quinazolines. 6.[1] Asymmetric Synthesis of (S)-(+)- and (R)-(-)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.
Grell, W., et al., "Repaglinide and Related Hypoglycemic Benzoic Acid Derivatives", J. Med. Chem., 1998, vol. 41, pp. 5219-5246.
Artico, M. et al., "Research on Compounds with Antiblastic Activity", Farmaco Ed. Sci. 1969, vol. 24, pp. 179-190.
Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.
Reppe, et al., "N-6-Aminohexyl-pyrrolidon", Justus Liebigs Ann. Chem. 1955, vol. 596, pp. 204.
Bouchet, P., et al., "σ Values of N-Substitutes Azoles", J. Chem. Soc. Perkin Trans., 1974, vol. 2, pp. 449-451.
Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.
Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.
Delande, S.A., "Heterocycles", Chemical Abstracts, American Chemical Society, 1979, vol. 90, pp. 663.

Bots, M., et al., Coagulation and Fibrinolysis Markers and Risk of Dementia, Haemostasis, vol. 28 (1998); pp. 216-222.
Benzakour, O., et al., "Cellular and molecular events in atherogenesis; basis for pharmocological and gene therapy approaches to stenosis," Cellular Pharmacology, 1996, vol. 3, pp. 7-22.
Kanthou, C., et al., "Cellular effects of thrombin and their signalling pathways," Cellular Pharmacology, vol. 2 (1995); pp. 293-302.
Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.
Tyrrell, D., et al., "Heparin in Inflammation: Potential Therapeutic Applications Beyond Anticoagulation," Advances in Pharmacology, vol. 46 (1999); pp. 151-208.
Smirova, I., et al., "Thrombin Is an Extracellular Signal that Activates Intracellular Death Protease Pathyways Inducing Apoptosis in Model Motor Neurons," J. Neurobiology, vol. 36 (1998); pp. 64-80.
Bono, F., et al., "Factor Xa Activates Endothelial Cells by a Receptor Cascade Between EPR-1 and PAR-2," Arterioscler Thromb Vasc Biol., Nov. 2000; pp. 1-6.
Lala, P. et al, "Role of Nitric Oxide in tumor progression: Lessons Learned from Experimental Tumors," Cancer and Metastasis Review, vol. 17, pp. 91-106 (1998).
Golub, T. et al., Molecular Classification of Cancer Science (1999), vol. 286, 531-537.
FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.
Ulllman's Encyclopedia of Industrial Chemistry, Fifth Revised Ed., Editors: Elvers, B., Hawkins, S., VCH Verlagsgesellschaft mbH, Weinheim, 1985-1996, Ch. 5, 488-506.
Zhu, B., Scarborough, R., "Recent Advances in Inhibitors of Factor Xa in the Prothrombinase Complex," Curr. Opinions Card. Pul. Ren. Inv. Drugs, 1:63-87 (1999).
Uzan, A., "Antithrombotic Agents," Emerging Drugs: The Prospect for Improved Medicines, 3: 189-208 (1998).
Kaiser, B., "Thrombin and Factor Xa Inhibitors," Drugs of the Future, 23: 423-426 (1998).
Al-Obeidi, F., Ostrem, J., "Factor Xa Inhibitors," Expert Opin. Therapeutic Patents, 9: 931-953 (1999).
Al-Obeidi, F., Ostrem, J., "Factor Xa Inhibitors by Classical and Combinatorial Chemistry," DDT, 3: 223-231 (May 1998).
Hauptmann, J. et al., "Synthetic Inhibitors of Thrombin and Factor Xa: From Bench to Bedside," Thrombosis Research, 93: 203-241 (1999).
Pschyrembel, Klinisches Worterbuch, 257. Auflage, 1994, Walter de Gruyter Verlag, p. 199-200, Stichwort "Blutgerinnung."
Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.
Pschyrembel, Klinisches Worterbuch, 257. Auflage, 1994, Walter de Gruyter Verlag, p. 610, Stichwort "Heparin."
Rompp Lexikon Chemie, Ver. 1.5, 1998, Georg Thieme Verlag Stuttgart, Stichwort "Heparin."
Pschyrembel, Klinisches Worterbuch, 257. Auflage, 1994, Walter de Gruyter Verlag, p. 292, Stichwort "Cumarinderivate."
Becker, M.R., et al., "Synthesis, Sar and in Vivo Activity of Novel Thienopyridine Sulfonamide Pyrrolidininones as Factor Xa Inhibitors," Bioorganic and Medicinal Chemistry Letters, 9: 2753-2758 (1999).
Linder, J., et al., "Delayed Onset of Inflammation in Protease-Activated Receptor-2-Deficient Mice," J. Immunology, 2000, pp. 6504-6510.
Cirino, G. et al. Inflammation-Coagulation Network: Are Serine Protease receptors the knot?; Tips; 200, vol. 21, pp. 170-172.
Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp. 5900-5908.

(56) References Cited

OTHER PUBLICATIONS

Caira, M. Crystalline Polymorphism of Organic Compounds. Springer Verlag Berlin Heidelberg 198, 1998, pp. 163-208.
Hancock, B. et al. Characteristics and Significance of the Amorphous State in Pharmaceutical Systems. Journal of Pharmaceutical Science. 86, 1 (Jan. 1997), pp. 1-12.
Chiou, W.L. et al. Pharmaceutical Applications of Solid Dispersion Systems. Journal of Pharmaceutical Sciences 60, (1971). 128-1302.
Ford, J.L. The Current Status of Solid Dispersions. Pharm Acta Helv. 61, (1986)69-88.
Rasenack, N. et al. Poorly Water-soluble Drugs for Oral Delivery—A Challenge for Pharmaceutical Development. Pharmazeutische Industrie 67, Nr. 5 (2005), 583-591.
Breitenbach, J. Melt extrusion: from process to drug delivery technology. European Journal of Pharmaceutics and Biopharmaceutics 54 (2002) 107-117.
Breitenbach, J. Feste Loesungen durch Schmelzextrusion—ein integriertes Herstellkonzept. Pharmazie in unserer Zeit 29 (2000), 46-49.
Stroke: Warning Signs and Tips for Prevention [online], retrieved Aug. 20, 2007 from the internet at http://familydoctor.org/online/famdocen/home/common/heartdisease/basics/290.html.
Kubitza, et al., Multiple dose escalation study Investigating the pharmacodyanamics, safety, and pharmacokinetics of BAY 59-7939 an oral, direct Factor Xa inhibitor in healthy male subjects, Blood, vol. 102:11:Nov. 16, 2003, p. 811a.
Kubitza, et al., Abstract 3010, Single dose escalation study investigating the pharmacodyanamics, safety, and pharmacokinetics of BAY 59-7939 an oral, direct Factor Xa inhibitor in healthy male subjects, Blood, vol. 102:11. Nov. 16, 2003, p. 813a.
Reppe, et al., Justus Liebigs Ann. Chem. 596, 1955, p. 209.
Wong et al., The Journal of Pharmacology and Experimental Therapeutics, vol. 295, No. 1 (2000) pp. 212-218.
Ross, Russell, "Atherosclerosis—An Inflammatory Disease," The New England Journal of Medicine; vol. 340, No. 2; pp. 115-126 (Jan. 14, 1999).
Perzborn, E. et al. In vitro and in vivo studies of the novel antithrombotic agent BAY 59-7939-an oral, direct Factor Xa inhibitor. Journal of Thrombosis and Haemostasis 3, 3, Mar. 2005, pp. 514-521.
Espinosa, G. et al. Thrombotic microangiopathic haemolytic anaemia and antiphospholipid antibodies. Annals of the Rheumatic Diseases, 63, 6, Jun. 2004, pp. 730-736.
Bonomini, V. et al. A New Antithrombotic Agent in the Treatment of Acute Renal Failure Due to Hemolytic-Uremic Syndrome and Thrombotic Thrombocytopenic Purpura. Nephron 37, 1984, 2, 144.
Sinha, U. et al. Antithrombotic and hemostatic capacity of factor Xa versus thrombin inhibitors in models of venous and arteriovenous thrombosis. European Journal of Pharmacology 2000, 395, 51-59.
Betz, A. Recent advances in Factor Xa inhibitors. Expert Opinion Ther. Patents 2001, 11, 1007-1017.
Tan, K.T. et al. Factor X inhibitors. Expert Opinion Investig. Drugs 2003, 12, 799-804.
Ruef, J. et al. New antithrombotic drugs on the horizon. Expert Opinion Investig. Drugs 2003, 12, 781-797.
Samama, M.L. Synthetic direct and indirect factor Xa inhibitors. Thromobis Research 2002, 106, V267-V273.
Quan, M.L. The race to an orally active Factor Xa inhibitor: Recent advances. Current Opinion in Drug Discovery & Development 2004, 7, 460-469.
The Ephesus Study, Blood 2000, 96, 490a.
The Penthifra Study, Blood 2000, 96, 490a.
The Pentamaks Study, Blood 2000, 96, 490a-491a.
The Pentathlon 2000 Study, Blood 2000, 96, 491a.
Leadley, R.J. Coagulation Factor Xa Inhibition: Biological Background and Rationale. Current Topics in Medical Chemistry 2001, 1, 151-159.
Gilligan, D.M. et al. The Management of Atrial Fibrillation. The American Journal of Medicine, vol. 101, (4) 1996, 413-421.
Kubitza, D. et al. Novel factor Xa inhibitors for prevention and treatment of thromboembolic diseases. Expert Opinion on Investig. Drugs, vol. 15, (8) 2006, pp. 843-855.
Williams, E.M. Vaughan. Classificating anti-arrhythimic drugs. In: Cardiac Arrythias—Proceedings of a symposium, sandoe E., soedertaeje: Astra (1970), pp. 449-469.
Lieberman et al., "Pharmaceutical Dosage Forms: Tablets", Marcel Dekker, Inc, 1980, vol. 1., pp. 109-124.
European Patent Office Communication of a Notice of Opposition dated Nov. 20, 2008, for EP Patent 1689370 B1.
Opposition to EP 1689370 B1 filed Nov. 12, 2008 by ratiopharm GmbH.
Reply to the Opposition to EP Patent 1689370 filed Jun. 15, 2009.
Reply to Patentee's Statement dated Jun. 15, 2009, filed in European Patent Office on Jan. 8, 2010.
Communication dated Mar. 31, 2010 in Opposition to EP 1 689 370B1.
Datasheet for Zyvoxid from South African Electronic Package Inserts, May 29, 2001.
Aulton, "Pharmaceutics: The Science of Dosage Form Design", 1998, pp. 136-137 and 154-156.
Pfizer, "Gebrauchsinformation: Information Fuer Den Anwender", Stand der Informationen: Oct. 2008.
"About FDA: The Biopharmaceutics Classification System (BCS) Guidance" of the US Food and Drug Administration, Jun. 3, 2009.
Pfizer, "Zyvoxid® Linezolid", Prescribing Information in Israel, Apr. 20, 2006.
"British Pharmacopoeia 2009," vol. I & II, General Notices Part II: Solubility.
Provisional Opinion of the Opposition Division of the European Patent Office in Opposition to EP Appl. 04 797 879, dated Jan. 14, 2011 (10 pages).
Welshman et al., "Linezolid Absolute Bioavailability and the Effect of Food on Oral Bioavailability", Biopharmaceutics & Drug Disposition, 2001, vol. 22, pp. 91-97.
Jain et al., "Pharmaceutical Product Development Technologies Based on the Biopharmaceutical Classification System", Pharmazie, 2009, vol. 64, pp. 483-490.
Aulton, "Pharmaceutics: The Science of Dosage Form Design", 2002 ($2^{nd}$ Ed.), pp. xiii, 6-9, 24-27, 113-114, 138, 142, 144, 253 and 273.
Bauer, K.H., et al., Lehrbuch der Pharmazeutische Technologie, 2002, pp. 220, 221 and 311, Publisher: Wissenschaftliche Verlagsgesllschaft mbH, Stuttgart.
Information from European Patent Office mailed Apr. 12, 2011 in Opposition to EP 1 689 370 rejecting Opposition over amended claims.
Kedvessy, G., et al., "Investigations into the absorption of some poorly water-soluble active ingredients from suspensions and tablets," Pharmazie, 1975, vol. 30, H. 7, pp. 476-478. (In German).
Lerk, C.F., et al., "In Vitro and In Vivo Availability of Hydrophilized Phenytoin from Capsules," Journal of Pharmaceutical Sciences, May 1979, vol. 68, No. 5, pp. 634-638.
Letter from ratiopharm to EPO dated Apr. 4, 2011 in Opposition to EP Patent 1 689 370.
Remington Pharmacia, Chapter 83, Preformulación, 1998, pp. 2231-2232.
Provisional minutes of the oral proceedings in the Opposition in the European Patent Office to EP 1 689 370 B (May 3, 2011).
Decision of the European Patent Office in the Opposition to EP 1 689 370B (May 16, 2011).
Lerk, et al., "Effect of Hydrophilization of Hydrophobic Drugs on Release Rate from Capsules," J. of Pharma. Sciences, 67(7), pp. 935-939 (1978).
Greaves, et al., "Novel Approaches to the Preparation of Low-Dose Solid Dosage Forms," Pharmaceutical Technology, pp. 60-64, Jan. 1995.
Eisenführ Speiser, "Einwendungen eines Dritten gemäß Artikel 115 EPÜ," which translated is Third Party Observation Pursuant to EPC Article 115, Mar. 17, 2014, submitted by Eisenführ Speiser to the European Patent Office in EP Application No. 1689370. (35 pages).
Amendment mailed Jul. 28, 2010, in U.S. Appl. No. 11/317,720.

(56) References Cited

OTHER PUBLICATIONS

Gandhi et al., "Extrusion and Spheronization in the Development of Oral Controlled-Release Dosage Forms", PSTT, 1999, vol. 2, No. 4, pp. 160.

Hilgers, et al., "Predicting Oral Absorption of Drugs: A case . . . ," 2003, Pharmaceutical Research, 20(8), pp. 1149-1155.

Kubitza et al., "Safety, Pharmacodynamics, and Pharmacokinetics of a Single Doses of BAY 59-7939, an Oral, Direct Factor Xa Inhibitor", Pharmacodynamics and Drug Action, 2005.

Lippold, "Controlled Release Products: Approaches of Pharmaceutical Technology," Oral Controlled Release Products: Therapeutic and Biopharmaceutic Assessment, editors U. Gundert-Remy and H. Moeller, 1989, pp. 39-57, Stuttgart, Germany.

Melia, "Hydrophilic Matrix Sustained Release Systems Based on Polysaccharide Carriers", Critical Reviews in Therapeutic Drug Carrier Systems, 1991, vol. 8, No. 4, pp. 395-421.

Muller, et al., "Emulsion and Nanosuspensions for the Formulation of Poorly Soluble Drugs," 1997, pp. 20.

Opposition of Ratiopharm GmbH to EP Patent 1 830 855 B1 filed Nov. 23, 2010.

Opposition of Sandoz GmbH to EP Patent 1 830 855 B1 filed Nov. 24, 2010.

Response to Final Office Action mailed Jan. 13, 2011, in U.S. Appl. No. 11/317,720.

Santus et al., "Osmotic Drug Delivery: A Review of the Patent Literature", Journal of Controlled Release, 1995, vol. 35, pp. 1-21.

Vazquez et al., "Influence of Technological Variables on Release of Drugs From Hydrophilic Matrices", Drug Development and Industrial Pharmacy, 1992, vol. 18 No. 11&12, pp. 1355-1375.

Verma et al., "Formulation Aspects in the Development of Osmotically Controlled Oral Drug Delivery Systems", Journal of Controlled Release, 2002, vol. 79, pp. 7-27.

Verma et al., "Osmotically Controlled Oral Drug Delivery", Drug Deveopment and Industrial Pharmacy, 2000, vol. 26, No. 7, pp. 695-708.

Advisory Action mailed Jan. 25, 2011, in U.S. Appl. No. 11/317,720.

Alderman, "A Review of Cellulose Ethers in Hydrophilic Materices for Oral Controlled-Release Dosage Forms", Int. J. Pharm. Tech. & Prod. Mfr., 1984, vol. 5, No. 3, pp. 1-9.

Verma, et al., "Osmotically controlled oral drug delivery," 2000, Drug Development and Industrial Pharmacy 26(7), pp. 695-708.

Weinz et al., "In vitro metabolism of BAY 59-7939—an oral, direct Factor Xa inhibitor", Drug Metabolism and Isotope Chemistry.

Bayer HealthCare's Reply to the Opposition to EP Patent 1830855 by ratiopharm GmbH, dated Jun. 28, 2011 with first auxiliary claim request (19 pages).

Office Action mailed Feb. 11, 2015, in U.S. Appl. No. 14/202,481.

Amendment mailed May 11, 2015, in U.S. Appl. No. 14/202,481.

Gao et al., "Fluid bed granulation of a poorly water soluble, low density, micronized drug: comparison with high shear granulation," International Journal of Pharmaceutics 237 (2002), pp. 1-14.

Eisenfuhr Speiser, "Einwendungen eines Dritten gemass Artikel 115 EPU," which translated is Third Party Observation Pursuant to EPC Article 115, dated Jun. 17, 2014, submitted by Eisenfuhr Speiser for client Helm AG to the European Patent Office in EP Application Publication No. EP1689370.

Herbert Lieberman and Leon Lachman (eds.), "Pharmaceutical Dosage Forms: Tablets", 1980, vol. 1, chapter 3 entitled "Compressed Tablets," pp. 109-124.

Dilip Parikh (ed.), "Handbook of Pharmaceutical Granulation Technology," 1997, pp. 7-9, published by Marcel Dekker, Inc., New York—Basel.

Anonymous, "Third Party Observations Under Article 115 EPC," filed against European Patent EP1689370, Jun. 26, 2014 (with cover letter from EP Board of Appeal forwarding for patentee on Jul. 1, 2014).

Weinz et al., "In vitro metabolism of BAY 59-7939—an oral, direct Factor Xa inhibitor", 7th International Meeting of the International Society for the Study of Xenobiotics; Vancouver, BC, Canada; Aug. 29-Sep. 2, 2004, ISSN: 0360-2532.

Bayer HealthCare's Reply to the Opposition to EP Patent 1830855 by ratiopharm GmbH, dated Jun. 28, 2011 with first auxiliary claim request (39 pages).

Benke et al., U.S. Appl No. 14/202,481, entitled "Process for the Preparation of a Solid, Orally Administrable Pharmaceutical Composition".

Declaration of Klaus Benke, Oct. 29, 2014, submitted in EPO Opposition to EP Patent 04797879.

Bayer Submission in EPO Opposition to EP Patent 04797879; dated Nov. 3, 2014.

Voight, R. "Pharmazeutische Technologie," Publisher: Deutscher Apotheker Verlag Stuttgart, 2000, pp. 166-167.

Herzfeldt, C., "Propädeutikum der Arzneiformenlehre, Galenik 1," Pulisher: Springer-Verlag, Berlin, 1992, pp. 133-135.

Minutes of the Oral Proceedings in Appeal of Opposition to EP Patent 04797879 dated Jun. 9, 2015; 6 pgs.

Bayer submission in EPO Opposition/Appeal to EP Patent 04797879 dated Apr. 13, 2015; 47 Pgs.

Ratiopharm GmbH Response Submission in EPO Opposition/Appeal to EP Patent 04797879, dated May 15, 2015; 33 Pgs.

Bayer Reply Submison in EPO Opposition/Appeal to EP Patent 04797879 dated May 29, 2015; 151 pgs.

Provisional Opinion in EPO OppositionlAppeal to EP Patent 04797879 dated Jun. 1, 2015; 36 pgs.

Bayer Submission in EPO Opposition/Appeal to EP Patent 04797879 dated Jun. 5, 2015; 8 pgs.

Minutes of the Oral Proceedings in Appeal of Opposition to EP Patent 04797879 dated Jun. 9, 2015; 3 pgs.

Notice of Allowance, U.S. Appl. No. 14/202,481 mailed Jul. 16, 2015.

English Translation of Granted Claims From KR10-1151117 Patent Dated May 22, 2012.

Petition Brief Filed by Hanmi Pharmaceutical Co., Ltd. at the Korean Intellectual Property Office Against KR Patent No. 10-1151117 on Mar. 10, 2015.

Korean Intellectual Property Office's Decision Dated Nov. 3, 2015 in Invalidity Action Filed by Hanmi Pharmaceutical Co., Ltd.

Translation of Petition Brief Filed by Ahngook Pharmaceutical Co., Ltd. at the Korean Intellectual Property Office Against KR Patent No. 10-1151117 on Mar. 27, 2015.

Response Brief Filed by Bayer at the Korean Intellectual Property Office on Oct. 16, 2015.

Comprehensive Brief Filed by Hanmi Pharmaceutical Co., Ltd. at the Korean Intellectual Property Office Against KR Patent No. 10-1151117 on Oct. 16, 2015.

Response Brief Filed by Bayer at the Korean Intellectual Property Office on Aug. 3, 2015 in Case No. 2015Dang770.

Presentation Made by Bayer to the Korean Intellectual Property Office at Oral Hearing on Sep. 24, 2015 in Case No. 2015Dang770.

Decision by the Technical Board of Appeal of the European Patent Office concerning EP Patent 1689370, mailed Mar. 23, 2016.

Appeal brief filed by Hanmi Pharmaceutical Co., Ltd. at the Korean Intellectual Property Office against Korean Patent No. 10-1151117 on Mar. 18, 2016.

Response brief filed by Bayer Intellectual Property GmbH at the Korean Intellectual Property Office on May 16, 2016 in Appeal of Patent Invalidation Case No. 2015Heo8455 (with six exhibits).

\* cited by examiner

SOLID, ORALLY ADMINISTRABLE PHARMACEUTICAL COMPOSITION

CROSS-REFERENCE TO RELATED APPLIATIONS

This application is the continuation of U.S. application Ser. No. 10/580,711, filed May 18, 2007, which is hereby incorporated herein by reference in its entirety, and which is the national stage application (under 35 U.S.C. §371) of PCT/EP2004/012897 filed Nov. 13, 2004, which claims benefit of German application 10355461.0 filed Nov. 27, 2003.

STATEMENT REGARDING FEDERALLY SPONSORED RESEARCH OR DEVELOPMENT

Not Applicable.

THE NAMES OF THE PARTIES TO JOINT RESEARCH AGREEMENT

Not Applicable.

INCORPORATED BY REFERENCE OF MATERIAL SUBMITTED ON A COMPACT DISC OR AS A TEXT FILE VIA THE OFFICE ELECTRONIC FILING SYSYTEM (EFS-WEB).

Not Applicable.

STATEMENT REGARDING PRIOR DISCLOSURES BY THE INVENTOR OR A JOINT INVENTOR

Not Applicable.

BACKGROUND OF THE INVENTION

1. Field of the Invention

The present invention relates to a process for the preparation of a solid, orally administrable pharmaceutical composition, comprising 5-chloro-N-({(5S)-2-oxo-3-[4-(3-oxo-4-morpholinyl)-phenyl]-1,3-oxanzolidin-5-yl}-methyl)-2-thiophenecarboxamide in hydrophilized form, and its use for the prophylaxis and/or treatment of diseases.

2. Description of Related Art Including Information Disclosed Under 37 CFR 1.97 and 1.98.

5-Chloro-N-({(5S)-2-oxo-3-[4-(3-oxo-4-morpholinyl)-phenyl]-1,3-oxazolidin-5-yl}-methyl-2-thiophenecarboxamide (I) is a low molecular weight, orally administrable inhibitor of blood clotting factor Xa, which can be employed for the prophylaxis and/or treatment of various thromboembolic diseases (for this see WO-A 01/47919, whose disclosure is hereby included by way of reference). If, below, the discussion is of the active compound (I), all modifications of 5-chloro-N-({(5S)-2-oxo-3-[4-(3-oxo-4-morpholinyl)-phenyl]-1,3-oxazolidin-5-yl}-methyl)-2-thiophenecarboxamide (I), and the respective hydrates are additionally included.

The active compound (I) has a relatively poor water solubility (about 7 mg/l). As a result of this, difficulties with the oral bioavailability and an increased biological variability of the absorption rate can result.

To increase the oral bioavailability, various concepts have been described in the past:

Thus, solutions of active compounds are frequently used which can be filled, for example, into soft gelatine capsules. On account of the poor solubility of the active compound (I) in the solvents used for this purpose, this option is not applicable, however, in the present case, since, in the necessary dose strength, capsule sizes would result which are no longer swallowable.

An alternative process is the amorphization of the active compound. Here, the solution method proves problematical, since the active compound (I) is also poorly soluble in pharmaceutically acceptable solvents such as ethanol or acetone. Amorphization of the active compound by means of the fusion method is also disadvantageous because of the high melting point of the active compound (about 230° C.), since an undesirably high proportion of breakdown components is formed during the preparation.

Furthermore, a process for the hydrophilization of hydrophobic active compounds as exemplified by hexobarbital and phenytoin has been described (Lerk, Lagas, Fell, Nauta, *Journal of Pharmaceutical Sciences* Vol. 67, No. 7, July 1978, 935-939: "Effect of Hydrophilization of Hydrophobic Drugs on Release Rate from Capsules"; Lerk, Lagas, Lie-A-Huen, Broersma, Zuurman, *Journal of Pharmaceutical Sciences* Vol. 68, No. 5, May 1979, 634-638: "In Vitro and In Vivo Availability of Hydrophilized Phenytoin from Capsules"). The active compound particles are blended here in a mixer with a methyl- or hydroxyethylcellulose solution with extensive avoidance of an agglomeration step and then dried. The active compound thus obtained is subsequently filled into hard gelatine capsules without further treatment.

BRIEF SUMMARY OF THE INVETNION

Surprisingly, it has now been found that a special treatment of the surface of the active compound (I) in the course of the moist granulation brings about improved absorption behaviour. The use of the active compound (I) in hydrophilized form in the preparation of solid, orally administrable pharmaceutical compositions leads to a significant increase in the bioavailability of the formulation thus obtained.

The present invention relates to a process for the preparation of a solid, orally administrable pharmaceutical composition comprising 5-chloro-N-({(5S)-2-oxo-3-[4-(3-oxo-4-morpholinyl)-phenyl]-1,3-oxazolidin-5-yl}-methyl)-2-thiophenecarboxamide in hydrophilized form, in which (a) first granules comprising the active compound (I) in hydrophilized form are prepared by moist granulation (b) and the granules are then converted into the pharmaceutical composition, if appropriate with addition of pharmaceutically suitable additives.

The moist granulation in process step (a) can be carried out in a mixer (=mixer granulation) or in a fluidized bed (=fluidized bed granulation); fluidized bed granulation is preferred.

In the moist granulation, the active compound (I) can either be introduced into the pre-mixture (original mixture) as a solid or it is suspended in the granulating liquid. Preferably, the active compound (I) suspended in the granulating liquid is introduced into the moist granulation (suspension process).

BRIEF DESCRIPTION OF THE SEVERAL VIEWS OF THE DRWAING(S)

Not applicable.

DETAILED DESCRIPTION OF THE INVENTION

In a preferred embodiment of the present invention, the active compound (I) is employed in crystalline form.

In a particularly preferred embodiment of the present invention, the crystalline active compound (I) is employed in micronized form. The active compound (I) in this case preferably has an average particle size $X_{50}$ of less than 10 µm, in particular between 1 and 8 µm, and $X_{90}$ (90% proportion) of less than 20 µm, in particular of less than 15 µm.

The granulating liquid used according to the invention contains a solvent, a hydrophilic binding agent and, if appropriate, a wetting agent. The hydrophilic binding agent is in this case dispersed in the granulating liquid or preferably dissolved therein.

The solvents used for the granulating liquid can be organic solvents, such as, for example, ethanol or acetone, or water or mixtures thereof. Preferably, water is used as a solvent.

The hydrophilic binding agents employed for the granulating liquid are pharmaceutically suitable hydrophilic additives, preferably those which dissolve in the solvent of the granulating liquid.

Preferably, hydrophilic polymers such as, for example, hydroxypropylmethylcellulose (HPMC), carboxymethylcellulose (sodium and calcium salts), ethylcellulose, methylcellulose, hydroxyethylcellulose, ethylhydroxyethylcellulose, hydroxypropylcellulose (HPC), L-HPC (low-substituted HPC), polyvinylpyrrolidone, polyvinyl alcohol, polymers of acrylic acid and its salts, vinylpyrrolidone-vinyl acetate copolymers (for example Kollidon® VA64, BASF), gelatine, guar gum, partially hydrolysed starch, alginates or xanthan are employed here. Particularly preferably, HPMC is employed as a hydrophilic binding agent.

The hydrophilic binding agent can be present here in a concentration of 1 to 15%. (based on the total mass of the pharmaceutical composition), preferably of 1 to 8%.

The optionally present wetting agents employed for the granulating liquid are pharmaceutically suitable wetting agents (surfactants). The following may be mentioned, for example:

sodium salts of fatty alcohol sulphates such as sodium lauryl sulphate, sulphosuccinates such as sodium dioctyl sulphosuccinate, partial fatty acid esters of polyhydric alcohols such as glycerol monostearate, partial fatty acid esters of sorbitan such as sorbitan monolaurate, partial fatty acid esters of polyhydroxyethylenesorbitan such as polyethylene glycol sorbitan monolaurate, monostearate or monooleate, polyhydroxyethylene fatty alcohol ethers, polyhydroxyethylene fatty acid esters, ethylene oxide-propylene oxide block copolymers (Pluronic®) or ethoxylated triglycerides. Preferably, sodium lauryl sulphate is employed as a wetting agent.

If required, the wetting agent is employed in a concentration of 0.1 to 5% (based on the total mass of the pharmaceutical composition), preferably of 0.1 to 2%.

In the pre-mixture (original mixture) of the moist granulation, further pharmaceutically suitable additives are present. The following may be mentioned, for example:

fillers and dry binding agents such as cellulose powder, microcrystalline cellulose, silicified microcrystalline cellulose, dicalcium phosphate, tricalcium phosphate, magnesium trisilicate, mannitol, maltitol, sorbitol, xylitol, lactose (anhydrous or as a hydrate, for example monohydrate), dextrose, maltose, sucrose, glucose, fructose or maltodextrins disintegration promoters (disintegrants) such as carboxymethylcellulose, croscarmellose (crosslinked carboxymethylcellulose), crospovidone (crosslinked polyvinylpyrrolidone), L-HPC (low-substituted hydroxypropylcellulose), sodium carboxymethyl starch, sodium glycolate of potato starch, partially hydrolysed starch, wheat starch, maize starch, rice starch or potato starch In the case of tablet formulations having modified (delayed) release of active compound, instead of the disintegration promoter (disintegrant) substances can be present which influence the release rate. The following may be mentioned, for example: hydroxypropylcellulose, hydroxypropyl-methylcellulose, methylcellulose, ethylcellulose, carboxymethylcellulose, galactomannan, xanthan, glycerides, waxes, acrylic and/or methacrylic acid ester copolymers with trimethylammonium methylacrylate, copolymers of dimethylaminomethacrylic acid and neutral methacrylic acid esters, polymers of methacrylic acid or methacrylic acid esters, ethyl acrylate-methyl methacrylate copolymers or methacrylic acid-methyl acrylate copolymers.

The granules obtained in process step (a) are subsequently converted into the pharmaceutical composition according to the invention in process step (b).

Process step (b) comprises, for example, tabletting, filling into capsules, preferably hard gelatine capsules, or filling as sachets, in each case according to customary methods familiar to the person skilled in the art, if appropriate with addition of further pharmaceutically suitable additives.

Pharmaceutically suitable additives which may be mentioned are, for example:

lubricants, glidants, flow regulating agents such as fumaric acid, stearic acid, magnesium stearate, calcium stearate, sodium stearyl fumarate, higher molecular weight fatty alcohols, polyethylene glycols, starch (wheat, rice, maize or potato starch), talc, highly disperse (colloidal) silica, magnesium oxide, magnesium carbonate or calcium silicate disintegration promoters (disintegrants) such as carboxymethylcellulose, croscarmellose (crosslinked carboxymethylcellulose), crospovidone (crosslinked polyvinylpyrrolidone), L-HPC (low-substituted hydroxypropylcellulose), sodium carboxymethyl starch, partially hydrolysed starch, wheat starch, maize starch, rice starch or potato starch The present invention further relates to a solid, orally administrable pharmaceutical composition, comprising 5-chloro-N-({(5S)-2-oxo-3-[4-(3-oxo-4-morpholinyl)-phenyl]1,3-oxazolidin-5-yl}-methyl)-2-thiophenecarboxamide (I) in hydrophilized form.

The solid, orally administrable pharmaceutical composition according to the invention by way of example and preferably comprises granules, hard gelatine capsules or sachets filled with granules, and tablets releasing the active compound (I) rapidly or in a modified (delayed) manner. Tablets are preferred, in particular tablets rapidly releasing the active compound (I). In the context of the present invention, rapid-release tablets are in particular those which, according to the USP release method using apparatus 2 (paddle), such as described in the experimental section in chapter 5.2.2., have a Q value (30 minutes) of 75%.

The active compound (I) can be present in the pharmaceutical composition according to the invention in a concentration of 0.1 to 60%, preferably in a concentration of 1 to 40%, based on the total mass of the formulation. Here, the dose of the active compound (I) is preferably 1 to 100 mg.

If appropriate, the granules of tablets according to the invention are coated in a further step under customary conditions familiar to the person skilled in the art. The coating is carried out with addition of customary coating and film-forming agents familiar to the person skilled in the art, such as hydroxypropylcellulose, hydroxypropylmethylcellulose, ethylcellulose, polyvinyl-pyrrolidone, vinylpyrrolidone-vinyl acetate copolymers (for example Kollidon® VA64, BASF), shellac, acrylic and/or methacrylic acid ester copolymers with trimethylammonium methylacrylate, copolymers of dimethylaminomethacrylic acid and neutral methacrylic acid esters, polymers of methacrylic acid or methacrylic acid esters, ethyl acrylate-methyl methacrylate copolymers, methacrylic acid-methyl acrylate copolymers, propylene glycol, polyethylene glycol, glycerol triacetate, triethyl citrate and/or colour additives/pigments such as, for example, titanium dioxide, iron oxide, indigotin or suitable colour lakes.

The present invention further relates to the use of the pharmaceutical composition according to the invention for the prophylaxis and/or treatment of diseases, in particular of thromboembolic diseases such as cardiac infarct, angina pectoris (including unstable angina), reocclusions and restenoses after an angioplasty or aortocoronary bypass, cerebral infarct, transitory ischemic attacks, peripheral arterial occlusive diseases, pulmonary embolisms or deep venous thromboses.

The invention is illustrated in greater detail below by means of preferred exemplary embodiments, to which, however, it is not restricted. If not stated otherwise, all quantitative data below relate to percentages by weight.

Experimental Section

1. Tablet Preparation Using Granules Comprising the Active Compound (I) in Hydrophilized Form/Fluidized Bed Granulation Process 1.1 Tablet Composition (in mg/Tablet)

| | |
|---|---|
| Active compound (I), micronized | 20.0 mg |
| Microcrystalline cellulose | 35.0 mg |
| Lactose monohydrate | 22.9 mg |
| Croscarmellose (Ac-Di-Sol ®, FMC) | 3.0 mg |
| Hydroxypropylmethylcellulose, 5 cp | 3.0 mg |
| Sodium lauryl sulphate | 0.5 mg |
| Magnesium stearate | 0.6 mg |
| Hydroxypropylmethylcellulose, 15 cp | 1.5 mg |
| Polyethylene glycol 3.350 | 0.5 mg |
| Titanium dioxide | 0.5 mg |
| | 87.5 mg |

1.2 Preparation

Hydroxypropylmethylcellulose (5 cp) and sodium lauryl sulphate are dissolved in water. The micronized active compound (I) is suspended in this solution. The suspension thus prepared is sprayed onto the original mixture of microcrystalline cellulose, lactose monohydrate and croscarmellose as a granulating liquid in the course of a fluidized bed granulation. After drying and sieving (0.8 mm mesh width) the resulting granules, magnesium stearate is added and mixed. The press-ready mixture thus obtained is compressed to give tablets having a 6 mm diameter and a fracture resistance of 50-100 N. The subsequent coating of the tablets is carried out using titanium dioxide, which is suspended in an aqueous solution of hydroxypropylmethylcellulose (15 cp) and polyethylene glycol.

2. Tablet Preparation Using Granules Comprising the Active Compound (I) in Hydrophilized Form/High-Speed Granulation Process 2.1 Tablet Composition mg/Tablet)

| | |
|---|---|
| Active compound (I), micronized | 5.0 mg |
| Microcrystalline cellulose | 40.0 mg |
| Lactose monohydrate | 33.9 mg |
| Croscarmellose (Ac-Di-Sol ®, FMC) | 3.0 mg |
| Hydroxypropylmethylcellulose, 3 cp | 2.0 mg |
| Sodium lauryl sulphate | 0.5 mg |
| Magnesium stearate | 0.6 mg |
| Hydroxypropylmethylcellulose, 15 cp | 1.5 mg |

-continued

| | |
|---|---|
| Polyethylene glycol 400 | 0.5 mg |
| Iron yellow | 0.1 mg |
| Titanium dioxide | 0.4 mg |
| | 87.5 mg |

2.2 Preparation

The substances cellulose, lactose monohydrate and croscarmellose employed are mixed in a high-speed mixer (original granule mixture), Hydroxypropylmethylcellulose (3 cp) and sodium lauryl sulphate are dissolved in water. The micronized active compound (I) is suspended in this solution. The suspension thus prepared is added to the original granule mixture as a granulating liquid and blended uniformly with the original granule mixture with the aid of the rapidly rotating stirrer. After thorough mixing has been carried out, the moist granules are sieved (4 mm mesh width) and dried in the fluidized bed. After sieving the dried granules (0.8 mm mesh width), magnesium stearate is added and mixed. The press-ready mixture thus obtained is compressed to give tablets having a 6 mm diameter and a fracture resistance of 50-100 N. The subsequent coating of the tablets is carried out using titanium dioxide and iron yellow, the pigments being suspended beforehand in an aqueous solution of hydroxypropylmethylcellulose (15 cp) and polyethylene glycol.

3. Preparation of Granules Comprising the Active Compound (I) in Hydrophilized Form and Filling as Sachets 3.1 Granule Composition (in mg/Sachet)

| | |
|---|---|
| Active compound (I), micronized | 50.0 mg |
| Mannitol | 662.0 mg |
| Croscarmellose (Ac-Di-Sol ®, FMC) | 15.0 mg |
| Hydroxypropylmethylcellulose, 5 cp | 15.0 mg |
| Sodium lauryl sulphate | 1.0 mg |
| Highly disperse silica (Aerosil ® 200, Degussa) | 2.0 mg |
| Strawberry flavouring, spray-dried | 5.0 mg |
| | 750.0 mg |

3.2 Preparation

Hydroxypropylmethylcellulose (5 cp) and sodium lauryl sulphate are dissolved in water. The micronized active compound (I) is suspended in this solution. The suspension thus prepared is sprayed onto the original mixture of mannitol and croscarmellose as a granulating liquid in the course of a fluidized bed granulation. After drying and sieving (0.8 mm mesh width) the resulting granules, highly disperse silica (Aerosil®) and strawberry flavouring are added and mixed. The mixture thus obtained is filled into sachet pouches to 750 mg with the aid of a sachet filling machine.

4. Preparation of Granules Comprising the Active Compound (I) in Hydrophilized Form and Filling into Hard Gelatine Capsules 4.1 Granule Composition (in mg/Capsule)

| | |
|---|---|
| Active compound (I), micronized | 20.0 mg |
| Microcrystalline cellulose | 30.0 mg |
| Lactose monohydrate | 79.5 mg |
| Maize starch | 25.0 mg |
| Hydroxypropylmethylcellulose, 5 cp | 4.5 mg |
| Sodium lauryl sulphate | 0.5 mg |
| Highly disperse silica (Aerosil ® 200, Degussa) | 0.5 mg |
| | 160.0 mg |

4.2 Preparation

Hydroxypropylmethylcellulose (5 cp) and sodium lauryl sulphate are dissolved in water. The micronized active compound (I) is suspended In this solution. The suspension thus prepared is sprayed onto the original mixture of microcrystalline cellulose, lactose monohydrate and maize starch as a granulating liquid in the course of a fluidized bed granulation. After drying and sieving (0.8 mm mesh width) the resulting granules, highly disperse silica (Aerosil®) is added and mixed. The mixture obtained is filled to 160 mg in each case into hard gelatine capsules of capsule size 2.

5. Comparison of Tablets with/without Hydrophilized Active Compound (I)

5.1 Tablet Composition, Preparation

In order to investigate the tablet properties and the improved bioavailability of formulations containing hydrophilized active compound (I), uncoated tablets having a 10 mg active compound content (I) of the following composition are prepared (in mg/tablet):

| | |
|---|---|
| Active compound (I), micronized | 10.0 mg |
| Microcrystalline cellulose | 40.0 mg |
| Lactose monohydrate | 27.9 mg |
| Croscarmellose (Ac-Di-Sol ®, FMC) | 3.0 mg |
| Hydroxypropylmethylcellulose, 5 cp | 3.0 mg |
| Sodium lauryl sulphate | 0.5 mg |
| Magnesium stearate | 0.6 mg |
| | 85.0 mg |

Tablet-A: prepared by direct tabletting without granulation
Tablet B: prepared by the fluidized bed granulation/suspension process described in 1.2

The mixture for tablet A and the granules for tablet B are in each case pressed to give tablets having a diameter of 6 mm and a fracture strength of about 70-80 N.

5.2 Tablet Properties 5.2.1 Disintegration Time in Water (USP Disintegration Tester, Erweka):
Tablet A: about 1.5 minutes
Tablet B: about 6.5 minutes 5.2.2 In-Vitro Release The amounts of active compound released based on the declared total content of the tablets are shown in Table I below:

TABLE 1

| | In-vitro release | | | |
|---|---|---|---|---|
| | 15 min | 30 min | 45 min | 60 min |
| Tablet A | 87% | 92% | 93% | 94% |
| Tablet B | 94% | 95% | 96% | 96% |

(USP paddle, 900 ml of acetate buffer pH 4.5+0.5% sodium lauryl sulphate, 75 rpm)

5.2.3 Bioavailability

For the investigation of the bioavailability, three dogs were in each case administered three tablets of A or three tablets of B in cross-over fashion. The corresponding pharmacokinetic parameters after oral administration of 3 mg of active compound (I)/kg are listed in Table 2 below:

TABLE 2

| Pharmacokinetic parameters of active compound (I) | | | | | | | | |
|---|---|---|---|---|---|---|---|---|
| | | Animal | | | Mean | S.D. | Mean | S.D. |
| | | 1 | 2 | 3 | geom. | geom. | arithm. | arithm. |
| Tablet A | | | | | | | | |
| AUC(0-24) | [mg · h/l] | 1.39 | 2.31 | 3.34 | 2.21 | 1.55 | 2.35 | 0.974 |
| AUC(0-24)$_{norm}$ | [kg · h/l] | 0.464 | 0.770 | 1.11 | 0.735 | 1.55 | 0.782 | 0.325 |
| $C_{max}$ | [mg/l] | 0.299 | 0.398 | 0.430 | 0.371 | 1.21 | 0.376 | 0.0684 |
| $C_{max, norm}$ | [kg/l] | 0.0997 | 0.133 | 0.143 | 0.124 | 1.21 | 0.125 | 0.0228 |
| $C(24)/C_{max}$ | [%] | 12.2 | 2.99 | 55.1 | 12.6 | 4.29 | 23.4 | 27.8 |
| $t_{max}$ | [h] | 1.00 | 1.50 | 0.750 | 1.04 | 1.42 | 1.08 | 0.382 |
| Tablet B | | | | | | | | |
| AUC(0-24) | [mg · h/l] | 2.82 | 3.03 | 3.73 | 3.17 | 1.16 | 3.19 | 0.476 |
| AUC(0-24)$_{norm}$ | [kg · h/l] | 0.938 | 1.01 | 1.24 | 1.06 | 1.16 | 1.06 | 0.159 |
| $C_{max}$ | [mg/l] | 0.478 | 0.513 | 0.321 | 0.428 | 1.29 | 0.437 | 0.102 |
| $C_{max, norm}$ | [kg/l] | 0.159 | 0.171 | 0.107 | 0.143 | 1.29 | 0.146 | 0.0341 |
| $C(24)/C_{max}$ | [%] | 26.4 | 1.17 | 93.4 | 14.2 | 9.53 | 40.3 | 47.7 |
| $t_{max}$ | [h] | 1.00 | 1.50 | 0.750 | 1.04 | 1.42 | 1.08 | 0.382 |

Result: In spite of slower disintegration (see 5.2.1) and very similar in-vitro release (see 5.2.2) of tablet B in comparison to tablet A, tablet B has marked advantages in absorption and thus a bioavailability increased by about 35%. At the same time, a marked decrease in the variability is to be noted. The only difference between tablet A and tablet B is the hydrophilization of the active compound (I) in tablet B with the aid of the suspension process in the course of the moist granulation.

The invention claimed is:

1. A process for the preparation of a solid, orally administrable pharmaceutical composition comprising an active compound (I) that is 5-chloro-N-({(5S)-2-oxo-3-[4-(3-oxo-4-morpholinyl)-phenyl]-1,3-oxazolidin-5-yl}-methyl)-2-thiophenecarboxamide in hydrophilized form, comprising the following steps:
   (a) first preparing granules comprising the active compound (I) in hydrophilized form using fluidized bed granulation for moist granulation;
   (b) and converting the granules into the pharmaceutical composition.

2. The process according to claim 1, wherein the active compound (I) is employed in crystalline form.

3. The process according to claim 2, wherein the active compound (I) is employed in micronized form.

4. The process according to claim 1, wherein the active compound (I) suspended in the granulating liquid is introduced into the moist granulation.

5. The process according to claim 1, wherein the resulting pharmaceutical composition is a tablet rapidly releasing the active compound (I).

6. A solid, orally administrable pharmaceutical composition comprising an active compound (I) that is 5-chloro-N-({(5S)-2-oxo-3-[4-(3-oxo-4-morpholinyl)-phenyl]-1,3-oxazolidin-5-yl}-methyl)-2-thiophenecarboxamide in hydrophilized form prepared by a process comprising the following steps:
   (a) first preparing granules comprising the active compound (I) in hydrophilized form using fluidized bed granulation for moist granulation;
   (b) and converting the granules into the pharmaceutical composition.

7. The pharmaceutical composition according to claim 6, comprising the active compound (I) in crystalline form.

8. The pharmaceutical composition according to claim 7, comprising the active compound (I) in micronized form.

9. The pharmaceutical composition according to claim 6, wherein the active compound (I) is present in a concentration of 1 to 60% based on the total mass of the composition.

10. The pharmaceutical composition according to claim 6, further comprising sodium lauryl sulphate as a wetting agent.

11. The pharmaceutical composition according to claim 10, wherein said sodium lauryl sulphate is present in a concentration of 0.1 to 5%, based on the total mass.

12. The pharmaceutical composition according to claim 6, further comprising hydroxypropylmethylcellulose as a hydrophilic binding agent.

13. The pharmaceutical composition according to claim 12, wherein said hydroxypropylmethylcellulose is present in a concentration of 1 to 15%, based on the total mass.

14. The pharmaceutical composition according to claim 6 that is in the form of a tablet.

15. The pharmaceutical composition according to claim 14 that is in the form of a rapid-release tablet.

16. The pharmaceutical composition according to claim 15, characterized in that the tablet is covered with a coating.

17. A method for the prophylaxis and/or treatment of thromboembolic diseases comprising administering an effective amount of the pharmaceutical composition of claim 6 to a patient in need thereof.

18. The process according to claim 1, wherein the granules are converted into the pharmaceutical composition with the addition of pharmaceutically suitable additives.

19. The process of claim 1, wherein the granules are converted into the pharmaceutical composition by tableting, filling into capsules, or filling into sachets.

20. The process according to claim 1, wherein the granules are converted into the pharmaceutical composition by a converting process selected from tableting, filling into capsules, and filling into sachets, and further wherein the converting process comprises adding pharmaceutically suitable additives.

21. The process according to claim 20, wherein the converting process is tableting.

22. The solid, orally administrable pharmaceutical composition of claim 6, wherein the granules are converted into the pharmaceutical composition with the addition of pharmaceutically suitable additives.

23. The solid, orally administrable pharmaceutical composition of claim 6, wherein the granules are converted into the pharmaceutical composition by tableting, filling into capsules, or filling into sachets.

24. The solid, orally administrable pharmaceutical composition of claim 6, wherein the granules are converted into the pharmaceutical composition by a converting process selected from tableting, filling into capsules, and filling into sachets, and further wherein the converting process comprises adding pharmaceutically suitable additives.

* * * * *